(12) United States Patent
Elster et al.

(10) Patent No.: US 6,987,897 B2
(45) Date of Patent: Jan. 17, 2006

(54) FIBER-OPTIC FLOW CELL AND METHOD RELATING THERETO

(75) Inventors: Jennifer L. Elster, Blacksburg, VA (US); Mark E. Jones, Blacksburg, VA (US); Charles D. Pennington, Blacksburg, VA (US); Joshua P. Averett, Radford, VA (US)

(73) Assignee: Luna Innovations Incorporated, Blacksburg, VA (US)

( * ) Notice: Subject to any disclaimer, the term of this patent is extended or adjusted under 35 U.S.C. 154(b) by 0 days.

(21) Appl. No.: 10/695,236

(22) Filed: Oct. 28, 2003

(65) Prior Publication Data

US 2004/0086216 A1    May 6, 2004

Related U.S. Application Data

(60) Provisional application No. 60/422,495, filed on Oct. 31, 2002.

(51) Int. Cl.
    *G02B 6/00*    (2006.01)
(52) U.S. Cl. .......................................... 385/12; 385/37
(58) Field of Classification Search ................. 385/12, 385/13, 37
    See application file for complete search history.

(56) References Cited

U.S. PATENT DOCUMENTS

| | | | |
|---|---|---|---|
| 5,216,312 A | 6/1993 | Baer et al. | |
| 5,359,681 A | 10/1994 | Jorgenson et al. | |
| 5,647,030 A | 7/1997 | Jorgenson et al. | |
| 5,738,825 A | 4/1998 | Rudigier et al. | |
| 5,814,565 A | 9/1998 | Reichert et al. | |
| 5,835,645 A | 11/1998 | Jorgenson et al. | |
| 5,864,641 A | 1/1999 | Murphy et al. | |
| 5,917,606 A * | 6/1999 | Kaltenbach | 356/440 |
| 6,067,216 A * | 5/2000 | Groger | 361/56 |
| 6,136,269 A * | 10/2000 | Winkler et al. | 422/61 |
| 6,137,576 A * | 10/2000 | Pauluth et al. | 356/517 |
| 6,200,814 B1 | 3/2001 | Malmqvist et al. | |
| 6,215,943 B1 * | 4/2001 | Crotts et al. | 385/137 |
| 6,439,055 B1 | 8/2002 | Maron et al. | |
| 6,526,188 B2 | 2/2003 | Dourdeville et al. | |
| 6,558,958 B1 * | 5/2003 | Pilevar et al. | 436/518 |
| 6,694,067 B1 * | 2/2004 | O'Keefe et al. | 385/12 |
| 2002/0034457 A1 * | 3/2002 | Reichert et al. | 422/82.11 |

\* cited by examiner

Primary Examiner—Juliana Kang
(74) Attorney, Agent, or Firm—Joy L. Bryant

(57) ABSTRACT

The present invention is for a fiber optic flow cell. The flow cell comprises a substrate having at least one sample channel and at least one optical fiber channel holder. At least one optical fiber is disposed within each optical fiber channel holder. Each optical fiber has at least one grating wherein each grating is in contact with each sample channel, defining a sensing area. At least one sample port is positioned in an operable relationship to at least one sample channel. Alternatively, at least one sample outlet is positioned in an operable relationship to at least one sample channel. The flow cell may be of a modular design providing a flow cell kit that contains pieces that may be assembled to form custom-made flow cells. The flow cell is used for conducting measurement studies on a sample.

44 Claims, 14 Drawing Sheets

FIBER-OPTIC FLOW CELL AND METHOD RELATING THERETO

CROSS-REFERENCE TO RELATED APPLICATIONS

This application claims the benefit of U.S. Provisional Patent Application Ser. No. 60/422,495, entitled "Device for Liquid and Air Sampling and Detection Using Optical Fiber-Based Sensors," filed Oct. 31, 2002, which is incorporated by reference herein in its entirety.

FIELD OF THE INVENTION

The present invention relates to flow cells. In particular, it relates to a flow cell having a grating-based optical fiber sensor incorporated therein.

BACKGROUND OF THE INVENTION

Flow cells have been constructed for liquid-phase measurements using fluorescent-based devices that require the sensor surface to be in contact with the environment. These flow cells are primarily designed to enhance the sensing characteristics of a particular component by blocking background light from influencing the sensor response. The device enclosure is constructed in a way to limit background light, a primary noise factor in fluorescent applications. Because the primary purpose of the cell is to control coupled light, the cell does not take into account rigid support for the optical fiber or additional processing needs such as mode stripping. In addition, flow cells have configurations that require external pumps or other methods to bring the external environment to the sensor as opposed to directly exposing the sensor to the external environment.

Crotts et al. (U.S. Pat. No. 6,215,943 B1) describe an optical fiber holder that allows a sample to be tested while avoiding strain and bending influences. The holder comprises a tube having a longitudinal axis, a first end for receiving an optical fiber and a recessed second end for protecting the optical fiber tip. An aperture is disposed along a length of the longitudinal axis of the tube for exposing the optical fiber to a sample. A change in a sample is determined by disposing an optical fiber device having a sensing element into the optical fiber holder. The optical fiber holder is then inserted into a vessel containing a sample and the sample is circulated past the sensing element. The problem with this device is that it requires that a large enough sample volume be available to submerge the device and to circulate the sample past the sensor. Therefore, small (microliter) samples cannot be used. In addition, there is no way to control the manner by which the sample contacts the sensor. This is of particular importance when one desires to conduct kinetic studies. Kinetic studies and studies where it is desirable to obtain results in real-time as various samples come into contact with one another are difficult to conduct with this device because the method of dipping is limited by diffusion. Moreover, this configuration is only applicable to large sample sizes. When sample sizes are on the microliter scale, the holder is reduced dimensionally and loses its structural rigidity and, hence, its capability to measure adequately.

Malmqvist et al. (U.S. Pat. No. 6,200,814 B1) provides a method and device for controlling a fluid flow over a sensing surface within a flow cell. The methods employ laminar flow techniques to position a fluid flow over one or more discrete sensing areas on the sensing surface of the flow cell. Such methods permit selective sensitization of the discrete sensing areas, and provide selective contact of the discrete sensing areas with a sample fluid flow. The method requires that the surface of the sensor be sensitized by activating the sensing surface such that it is capable of specifically interacting with a desired analyte. The sensor device comprises a flow cell having an inlet end and an outlet end; at least one sensing surface on a wall surface within the flow cell located between the inlet and outlet ends; wherein the flow cell has at least two inlet openings at the inlet end, and at least one outlet opening at the outlet end, such that separate laminar fluid flows entering the flow cell through the respective inlet openings can flow side by side through the flow cell and contact the sensing surface. In this aspect, the flow cell and the sensing surface are one in the same. In another aspect of the invention, the sensor system comprises a flow cell having an inlet end and an outlet end; at least one sensing area on a sensing surface within the flow cell between the inlet and outlet ends; the flow cell having at least two inlet openings at the inlet end, and at least one outlet opening at the outlet end; means for applying laminar fluid flows through the inlet opening such that the laminar fluid flows pass side by side through the flow cell over the sensing surface; means for varying the relative flow rates of the laminar flows of fluids to vary the respective lateral extensions of the laminar flows over the sensing surface containing the sensing area or areas; and, detection means for detecting interaction events at the sensing area or areas. These flow cells are designed such that the sensing surface is a part of the wall surface within the flow cell. When the sensor is part of the flow cell wall, there is no way to route an optical fiber. Thus, the flow cell design does not allow incorporation of an optical fiber sensor.

Jorgenson et al. (U.S. Pat. Nos. 5,359,681; 5,647,030; and 5,835,645) disclose a fiber optic sensor which detects a sample in contact with the sensor by surface plasmon resonance (SPR) measurements. The sensor includes a surface plasmon supporting metal layer in contact with an exposed portion of the optical fiber core. Detection of a sample with the fiber optic SPR sensor is made, in part, by contacting the sample with the sensing area of the optical fiber. The sensing area is made by exposing a portion of the optical fiber core by removal of the surrounding cladding or cladding/buffer layers, and adhering an SPR supporting metal layer to the exposed optical fiber core. The SPR supporting metal layer of the optical fiber is then exposed to the sample of interest, and the refractive index of the sample is determined. The problem with this configuration is that it is difficult to keep the optical fiber straight while mass producing the flow cell with consistency. Moreover, the invention does not address a method for optimizing sampling.

An object of the present invention is to provide a flow cell that allows for various studies to be conducted on a sample or a variety of samples and sample combinations.

Another object of the invention is to provide a flow cell that employs a grating-based optical fiber sensor system.

Another object of the invention is to provide a flow cell that is capable of operation under varying flow rates with varying sample sizes.

Another object is to present a flow cell that permits measurement of reaction rates.

Another object of the invention is to provide a flow cell that is easy to manufacture and assemble with consistency.

Another object of the invention is to provide a flow cell that can be easily modified to achieve the desired testing apparatus.

Another object of the invention is to provide a flow cell design that provides the flexibility to increase the number of sample channels without compromising the ability of the sensors within the flow cell to make accurate measurements.

SUMMARY OF THE INVENTION

By the present invention, a flow cell is presented. The flow cell comprises a substrate having at least one sample channel and at least one optical fiber channel holder. At least one optical fiber is disposed within each optical fiber channel holder. Each optical fiber has at least one grating. Each optical fiber grating is in contact with each sample channel, defining a sensing area. At least one sample port is positioned in an operable relationship to at least one sample channel.

In a further embodiment of the invention, the flow cell has at least one sample outlet positioned in an operable relationship to at least one sample channel. The flow cell may be of a monolithic or piece-like structure. A flow cell kit contains at least two mating pieces that may be reconfigured in a number of arrangements depending on the desired application. The flow cell is used for conducting measurement studies on a neat sample or a complex mixture on a range of sample sizes, including samples of less than 100 microliters.

An advantage to these arrangements is that the optical fiber channel has sections in the flow cell where the optical fiber is isolated from the sample channel. This permits easy manufacturing of the flow cell without disturbing the configuration of the sample channel.

Additional objects and advantages of the invention will be set forth in part in the description which follows, and in part will be obvious from the description, or may be learned by practice of the invention. The objects and advantages of the invention will be obtained by means of instrumentalities in combinations particularly pointed out in the appended claims.

BRIEF DESCRIPTION OF THE DRAWINGS

The accompanying drawings illustrate a complete embodiment of the invention according to the best modes so far devised for the practical application of the principles thereof, and in which.

DETAILED DESCRIPTION OF THE PREFERRED EMBODIMENTS

Figure 1:
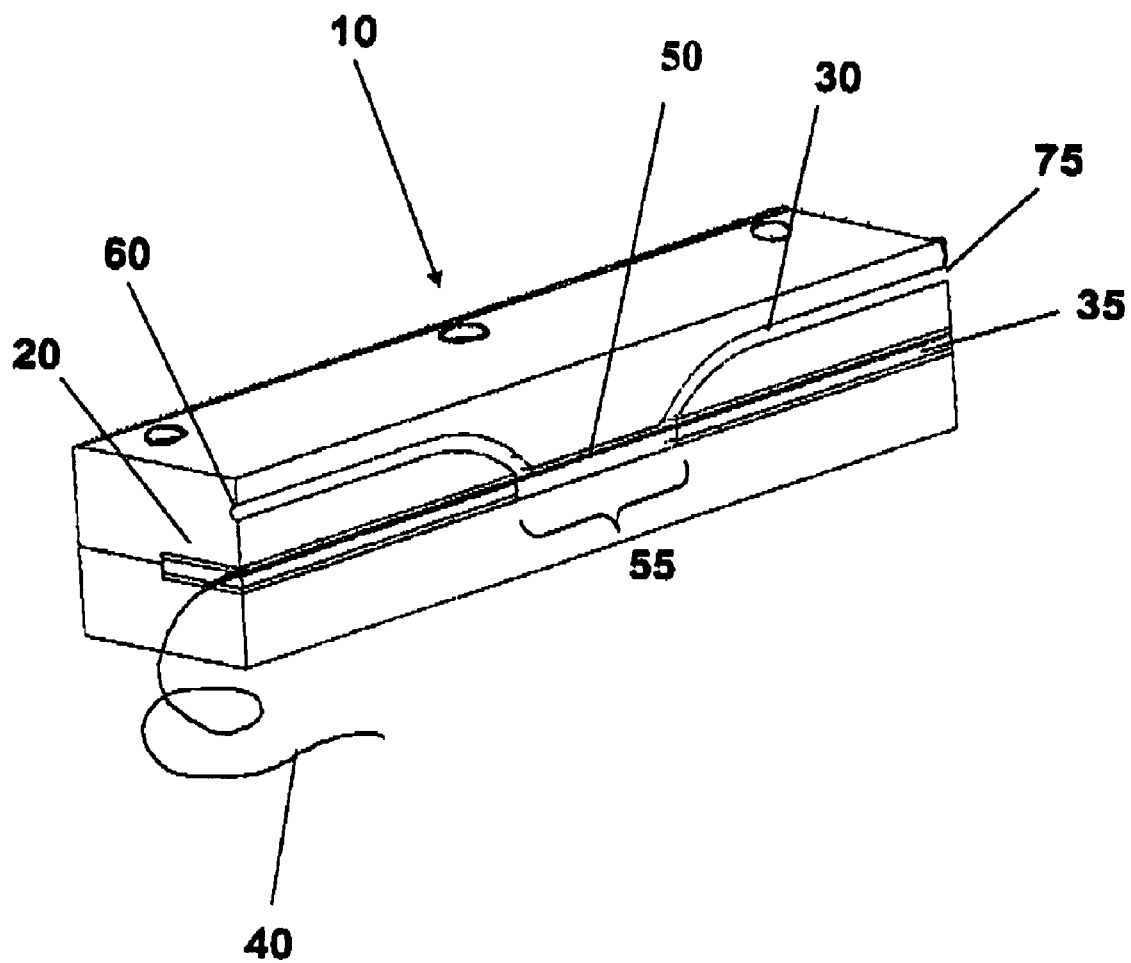
FIG. 1 is a cross sectional view of a flow cell embodiment having two sample ports that act as either an inlet and/or an outlet; a single sample channel; and a single optical fiber channel holder.

Referring now to the drawings, where similar parts are numbered the same, FIG. 1 depicts a simple embodiment of the invention where the flow cell 10 comprises a substrate 20 having at least one sample channel 30 and at least one optical fiber channel holder 35 disposed therein. For the purpose of this application and the appended claims, an optical fiber channel bolder is a holder that is capable of achieving precision alignment and consistent tension on the optical fiber. At least one optical fiber 40 is disposed within each optical fiber channel holder 35. The optical fiber 40 has at least one grating 50 disposed therein. The optical fiber channel holder 35 is designed to come into contact with the sample channel 30 at the points along the optical fiber where each optical fiber grating 50 is located. These points define a sensing area 55. At least one sample port 60 is positioned in an operable relationship to at least one sample channel 30 to permit introduction of a sample into the sample channel. A sample outlet 75 is in fluid connection with the sample channel 30 such that the sample is removed from the flow cell through the sample outlet 75. When the flow cell has no sample outlet, the sample is introduced into and exits from the flow cell through the sample port 60. The sample port 60 is positioned in an operable relationship to the sample channel 30 such that the sample may easily flow into the sample channel. In one embodiment of the invention, where the flow cell comprises more than one sample port, at least one sample port is plugged with a gas permeable material that allows air to escape as a sample is introduced into another sample port. Alternatively, a pump is attached to at least one sample port to serve as a means for either drawing or pushing the sample through the flow cell. Lastly, the sample port may serve as an exit port for the sample after it flows through the flow cell. Multiple sample ports may be employed when the user desires to introduce multiple samples into the flow cell. Alternatively, a pipette tip is formed on the sample port for drawing fluid samples into the sample channel and through the substrate. This is especially desirable when a microtiter plate arrangement is employed.

The sample channel is capable of being modified to achieve the desired sample delivery volume to the sensing area (preferably less than 100 microliters). The sample channel 30 is depicted in its preferred configuration where the sample channel is curved to provide optimal fluid flow within the sensor area. The curved shape allows the flow to be laminar, thus eliminating dead volumes. However, various geometries may be employed to enhance downstream and upstream flow of the sample. Alternatively, the sample channel 30 may also be straight to easily prevent samples from being trapped in the flow cell provided it is in contact with the grating portion of the optical fiber.

The optical fiber 40 is positioned within an optical fiber channel holder 35. Each optical fiber has a grating 50. The portion of the optical fiber having the grating 50 is positioned within the optical fiber channel holder 35 so that the grating 50 is in contact with the sample channel 30, defining a sensing area 55. This is the area where the sample contacts the optical fiber. The amount of sample flowing into the sensing area is controlled by modifying the dimensions of the sample channel by using different geometries. The optical fiber has, at a minimum, one grating disposed therein. The grating is either a Bragg grating or a long period grating, depending on the sample under test. More than one grating is disposed within the optical fiber when multiple test points are desired. When multiple gratings are disposed within the optical fiber, the optical fiber channel holder is configured such that each grating contacts the sample channel. Moreover, the optical fiber may be pre-treated with a reactive coating prior to insertion into the optical fiber channel holder. Reactive coatings are those coatings that are capable of undergoing a change when exposed to a specific parameter such that it causes the long period grating to produce a wavelength transmission spectrum functionally dependent on the change which takes place. These types of coatings are described in U.S. Pat. No. 5,864,641 to Murphy et al. which is hereby incorporated by reference in its entirety. Alternatively, the optical fiber may be treated in-situ by flowing a sample containing a reactive species over the optical fiber grating prior to introducing the sample into the flow cell. The optical fiber is connected to an optical light source and a detector using procedures known to those of skill in the art.

The design of the flow cell of the present invention overcomes the problem of Crotts et al. where large sample sizes are required. The novelty of the invention lies in the optical fiber channel holder 35 which helps the optical fiber sustain a linear shape and avoid possible distortion when it comes into contact with a sample. This aids in preventing optical distortions that result when the optical fiber is subject to sudden movements experienced when various samples come into contact with the optical fiber. This design is preferred over a design where the optical fiber is disposed within the sample channel because the optical distortions are reduced if not eliminated. Moreover, the optical fiber channel holder enables the optical fiber to be routed through the flow cell and facilitates alignment and simplifies fabrication procedures such that the configuration of the sample channel is not disturbed.

The substrate 20 gives rise to the overall shape of the flow cell 10 and is either a monolithic structure or a piece-like structure. In the case of a monolithic structure, the substrate is pre-cast or a solid piece that has been bored-out to provide at least one sample channel 30, at least one optical fiber channel holder 35, and at least one sample port 60. The flow cell 10 is any shape suitable for the desired application. In particular, the flow cell is either a cylinder or a planar (meaning 2-dimensional) structure.

Figure 2A:
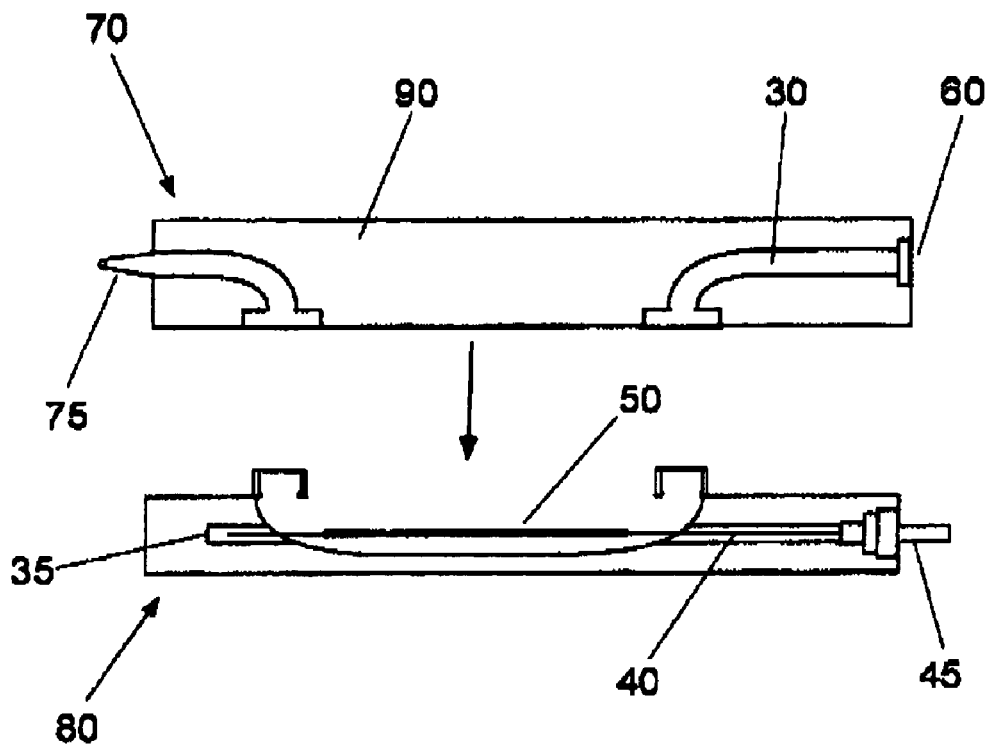
FIG. 2A is a cross-sectional view of the flow cell having two mating pieces.
Figure 2B:
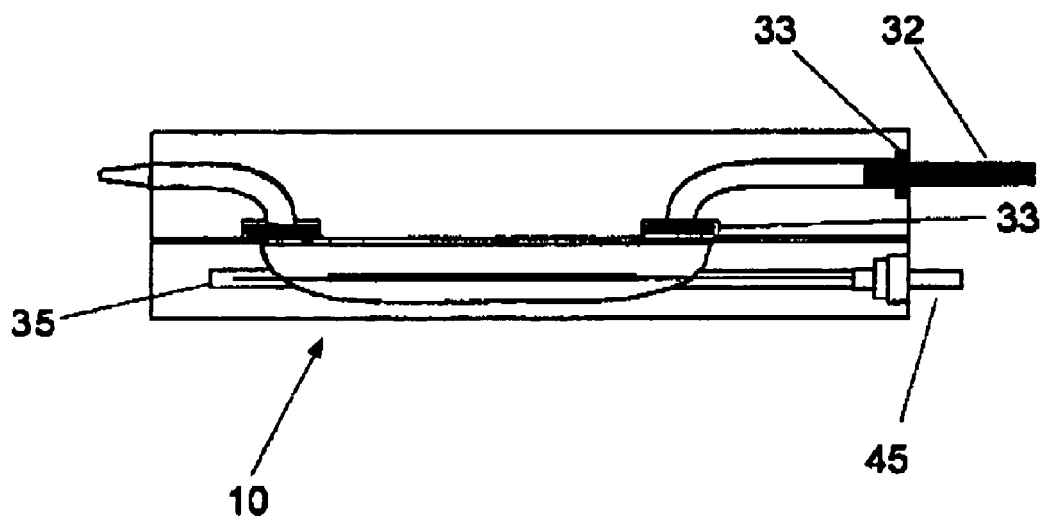
FIG. 2B is a cross-sectional view of the flow cell assembly when the two mating pieces are assembled together.

FIGS. 2A and 2B depict a flow cell 10 comprised of two mating pieces 70, 80. The upper portion 70 of the mating pieces contains at least one sample channel 30 and at least one sample port 60. FIGS. 2A and 2B show a preferred embodiment where there is a sample outlet 75 in fluid connection with the sample channel 30 such that the sample is removed from the flow cell through the sample outlet 75. The lower portion 80 of the mating pieces comprises at least one optical fiber channel holder 35 having an optical fiber 40 with a grating 50 disposed therein, positioned within the optical fiber channel holder 35. The optical fiber channel holder 35 is, in this instance, drilled out of the base such that it is essentially parallel to the sensing area. The figures also depict an embodiment where an optical fiber connector 45 is disposed within the flow cell and forms an input/output connection with the optical fiber. FIG. 2B shows a further embodiment of the invention where an injection port 32 has been incorporated with the sample port for introduction of a sample by injection. Thus, the flow cell has both an optical and a fluid connection within it. FIG. 2B depicts the structure of the flow cell when the mating pieces have been assembled together. The resulting structure may be of any geometric shape known to those of skill in the art. Preferably, the mating pieces give rise to a cylinder or planar structure. When the need arises, one may incorporate various sealing means, such as gaskets, to prevent leakage. FIG. 2B shows a sealing means 33 disposed at various junctures in the flow cell to prevent fluid leakage. Such sealing means may be of any means known to those of skill in the art such as gaskets, adhesives, and various sealing compounds.

Figure 3:
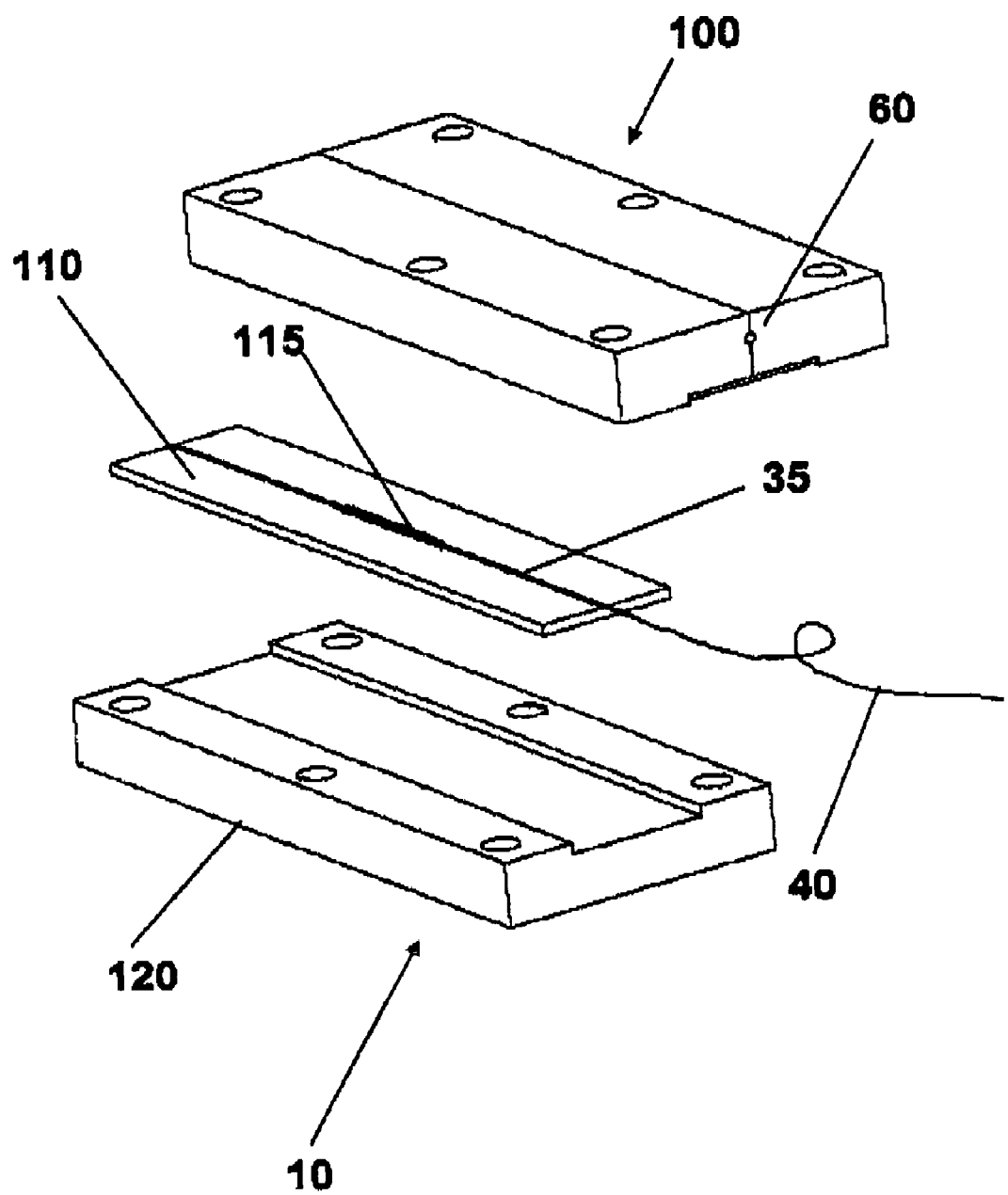
FIG. 3 is a cross-sectional view of the flow cell having three mating pieces.

FIG. 3 depicts an alternative embodiment of the flow cell 10 comprised of three mating pieces. In this embodiment, there is an upper section 100 containing at least one sample channel (not shown) and at least one sample port 60. This portion is counter-sunk to permit critical alignment of the optical fiber channel holder 35 with the sample channel. In the middle section 110, there is the optical fiber channel holder 35 having the optical fiber 40 disposed therein. The optical fiber channel holder 35 is configured to allow a space defining a sensing area 115 where the grating portion of the optical fiber 40 is located. The optical fiber channel holder is designed such that the sensing area and flow cell walls are close to the fiber for diffusion purposes. The lower section 120 of the flow cell serves as a support or base for the assembly. As with the upper portion, the lower section 120 is also counter-sunk to permit critical alignment of the optical fiber channel holder 35 with the sample channel. The flow cell assembly is joined and held together by a fastener. Any fastener known to those of skill in the art may be used. Examples of such fasteners include but are not limited to: screws; nuts and bolts; male-female connectors that are fabricated as part of the substrate; rivets; welds; adhesives; straps; crimp connectors such as bent wire; bands fabricated from rubber, metal, plastic; and clamps such as C-clamps. The use of multiple mating pieces allows the user to modify the flow cell or reconfigure it. For example, an upper section containing a single sample channel having one sample port may be substituted with an upper section having multiple sample channels having either one or multiple sample ports. If desired, the upper section may also contain a sample outlet or multiple sample outlets so the sample is removed from the flow cell through an outlet other than the sample port. Alternatively, the middle section may be exchanged to match the number of sample channels of the upper section or may provide a single sensing area where many samples converge. When the need arises, one may incorporate various sealing means, such as gaskets, to prevent leakage. Because of the versatility afforded by having a piece-like structure, a flow cell kit is provided that allows the user to design custom flow cells depending on the application. The kit configuration makes the flow cell easy to clean. The ability to disassemble the flow cell easily allows for the user to apply various coatings to the cell that can be removed without causing damage to the flow cell. A flow cell comprised of mating pieces provides a significant advantage over the prior art flow cells because it is easy to clean; can be easily converted for a particular application; provides consistent manufacturing and test results; and provides the flexibility to increase the number of sample channels without compromising the measurements made in the sensing area.

Figure 4:
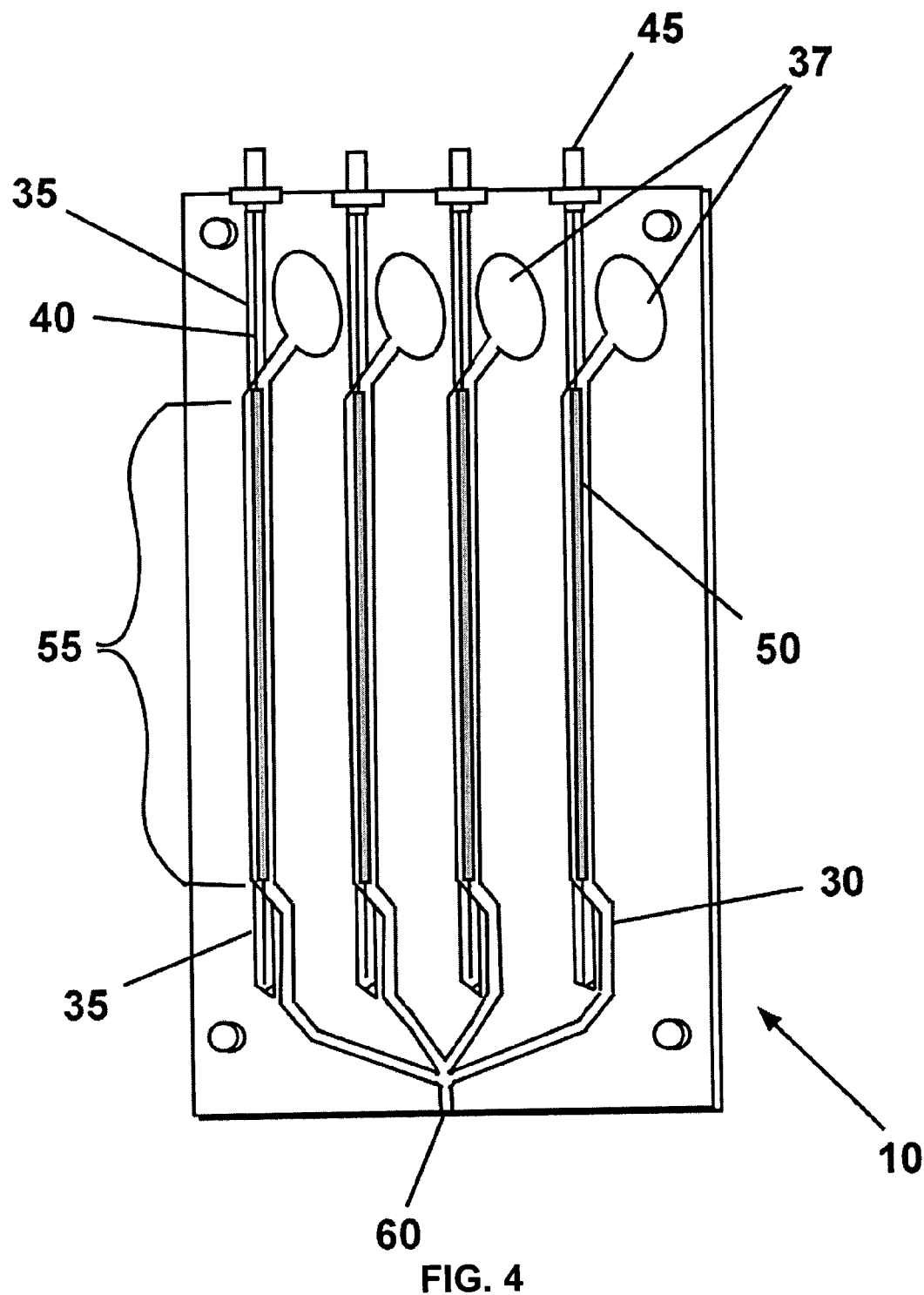
FIG. 4 is a cross-sectional view of the flow cell having a single sample port and a plurality of sample channels.
Figure 5:
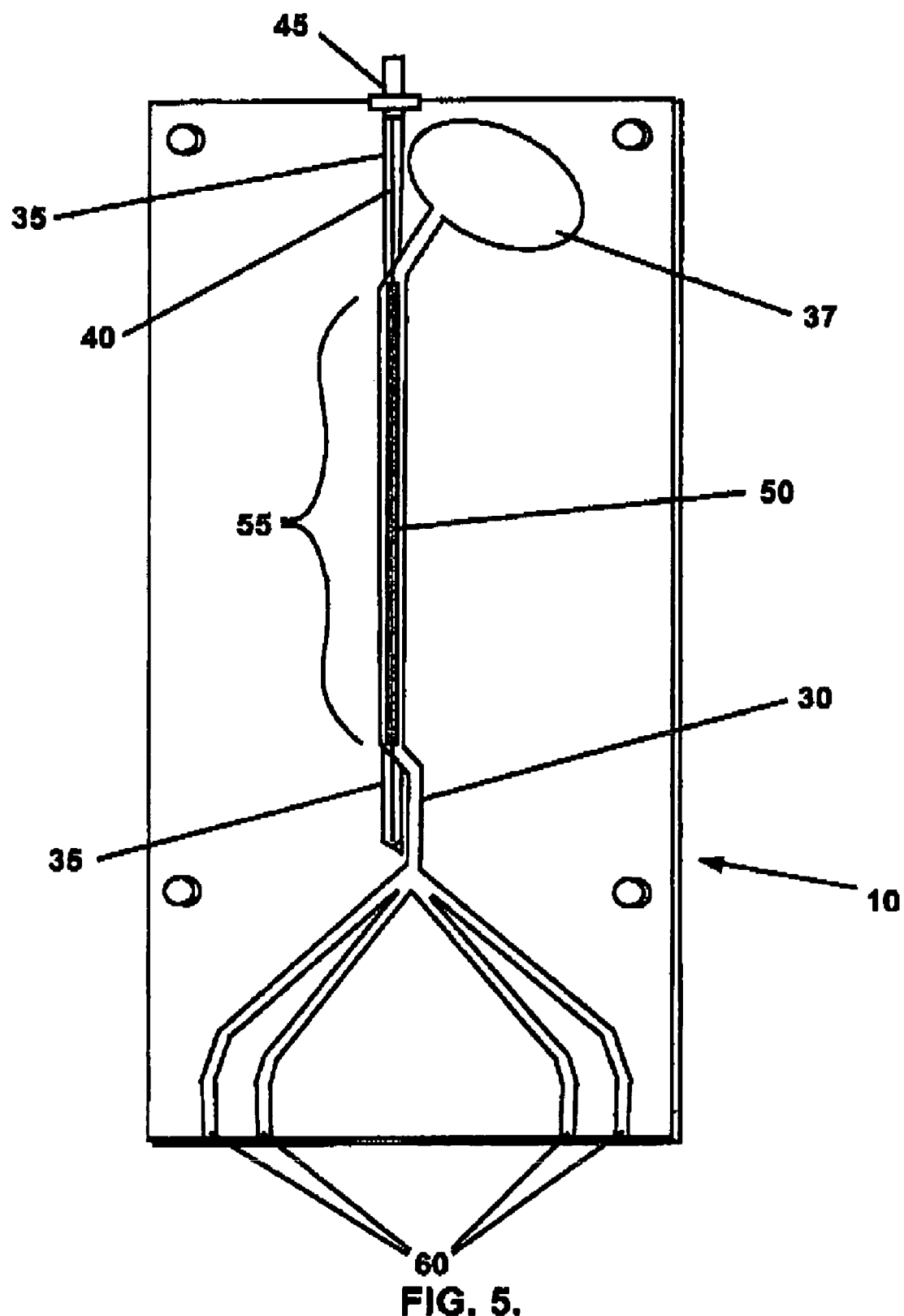
FIG. 5 is a cross-sectional view of the flow cell having a plurality of sample ports, a single sample channel, and a single sample outlet.

FIGS. 4 and 5 show alternative embodiments of the invention where the number of sample ports and sample channels are varied and the sample port serves as both an inlet and an outlet for the sample. In these configurations, the sample channel 30 terminates with a sample reservoir 37 This permits the sample to be contained within the flow cell after it has passed through the sensing area 55. FIG. 4 depicts an embodiment where there is one sample port 60 and a plurality of sample channels 30. In this arrangement, the sample enters and exits the flow cell 10 through the sample port 60. The optical fiber 40 is disposed within the optical fiber channel holder 35. Sample measurements are made in the sensing area 55 where the optical fiber grating 50 is in close proximity to the sample channel 30. FIG. 5 shows an alternative embodiment that allows samples to be mixed within the flow cell 10. In this embodiment, a plurality of sample ports 60 are provided but only one sample channel 30, terminating with a sample reservoir 37, is provided. The optical fiber 40 is disposed within the optical fiber channel holder 35. A plurality of samples are introduced through the sample ports 60, mixed in the sample channel 30, and detected in the sensing area 55 of the flow cell where the grating 50 is in close proximity to the sample channel. The mixed sample is removed from the flow cell through the sample ports 60 upon completion of the data collection process. Both figures depict a preferred embodiment where an optical fiber connector 45 is attached to an end of the optical fiber 40.

Figure 6:
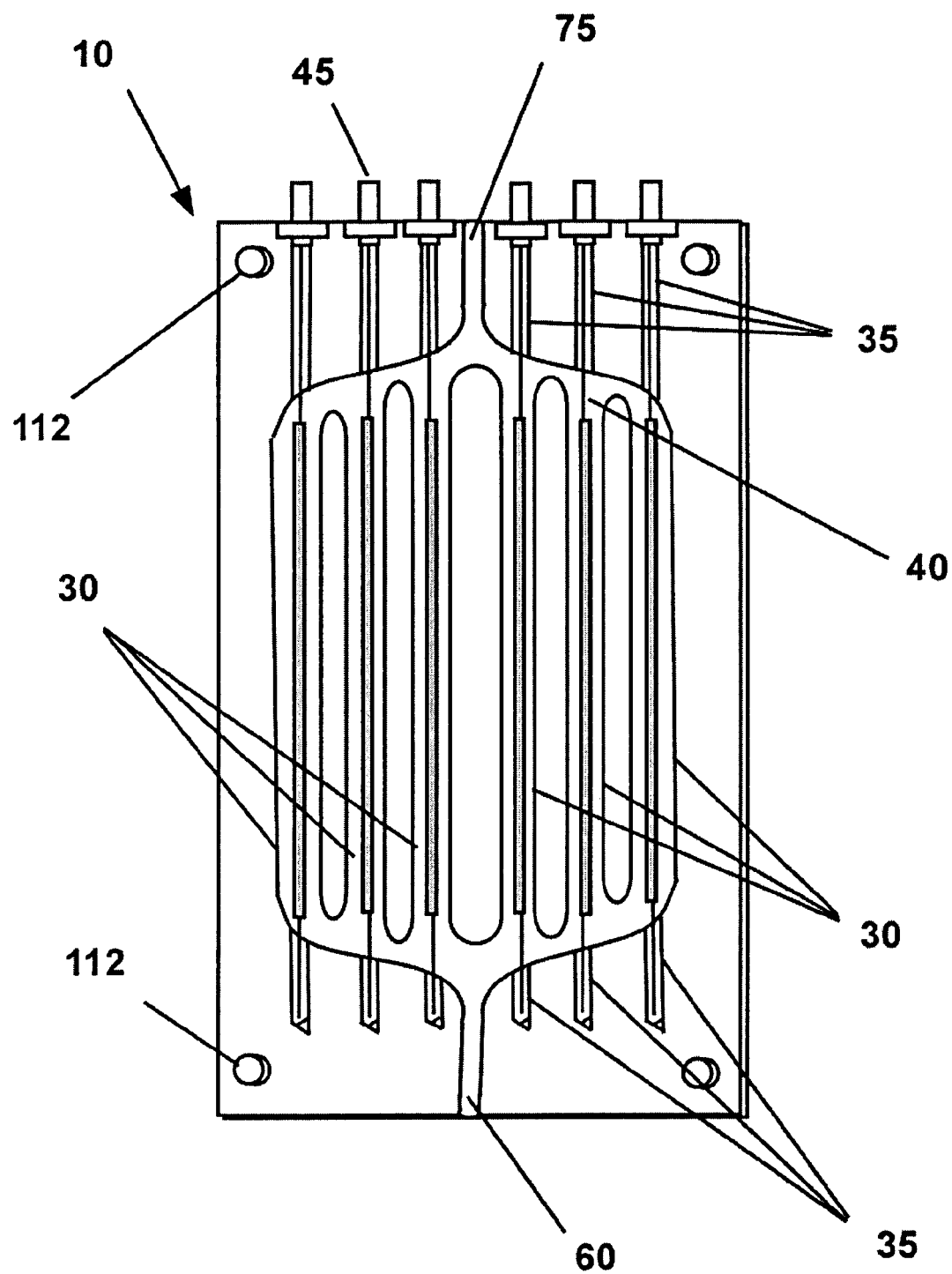
FIG. 6 is a cross-sectional view of the flow cell having one sample port, a plurality of sample channels, and one sample outlet.
Figure 7:
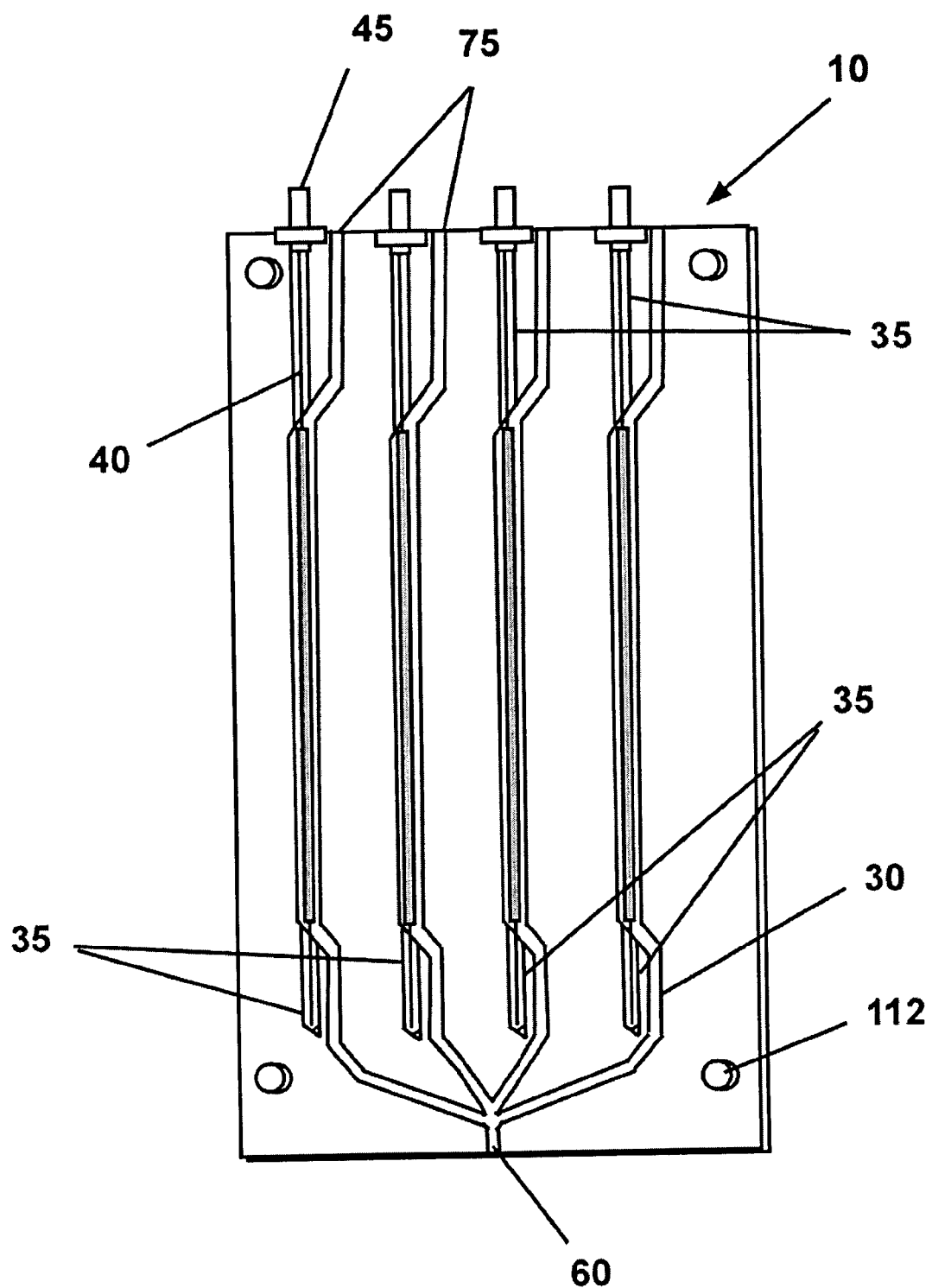
FIG. 7 is a cross-sectional view of the flow cell having one sample port, a plurality of sample channels, and a plurality of sample outlets.
Figure 8:
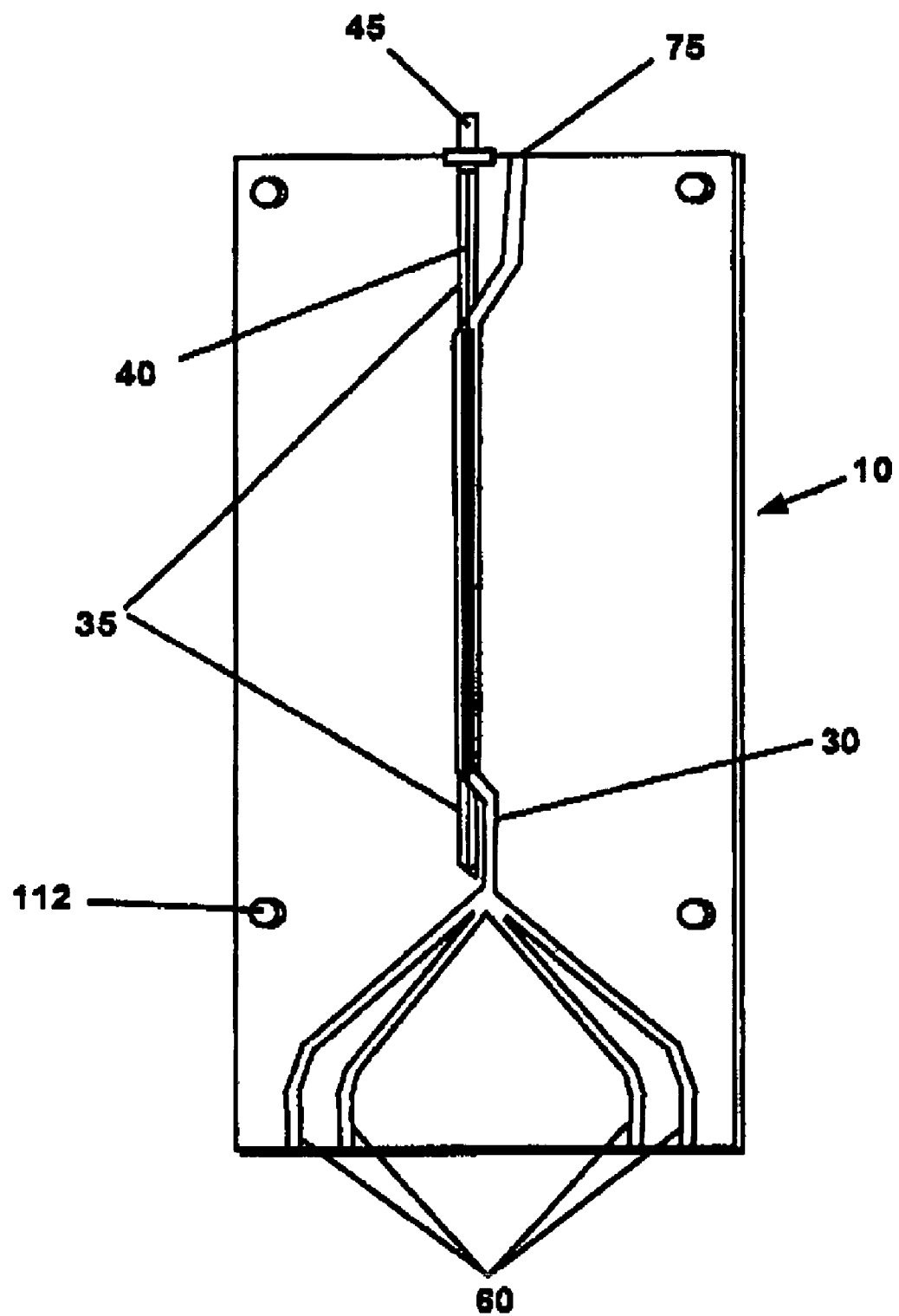
FIG. 8 is a cross-sectional view of the flow cell having a plurality of sample ports, one sample channel, and one sample outlet.
Figure 9:
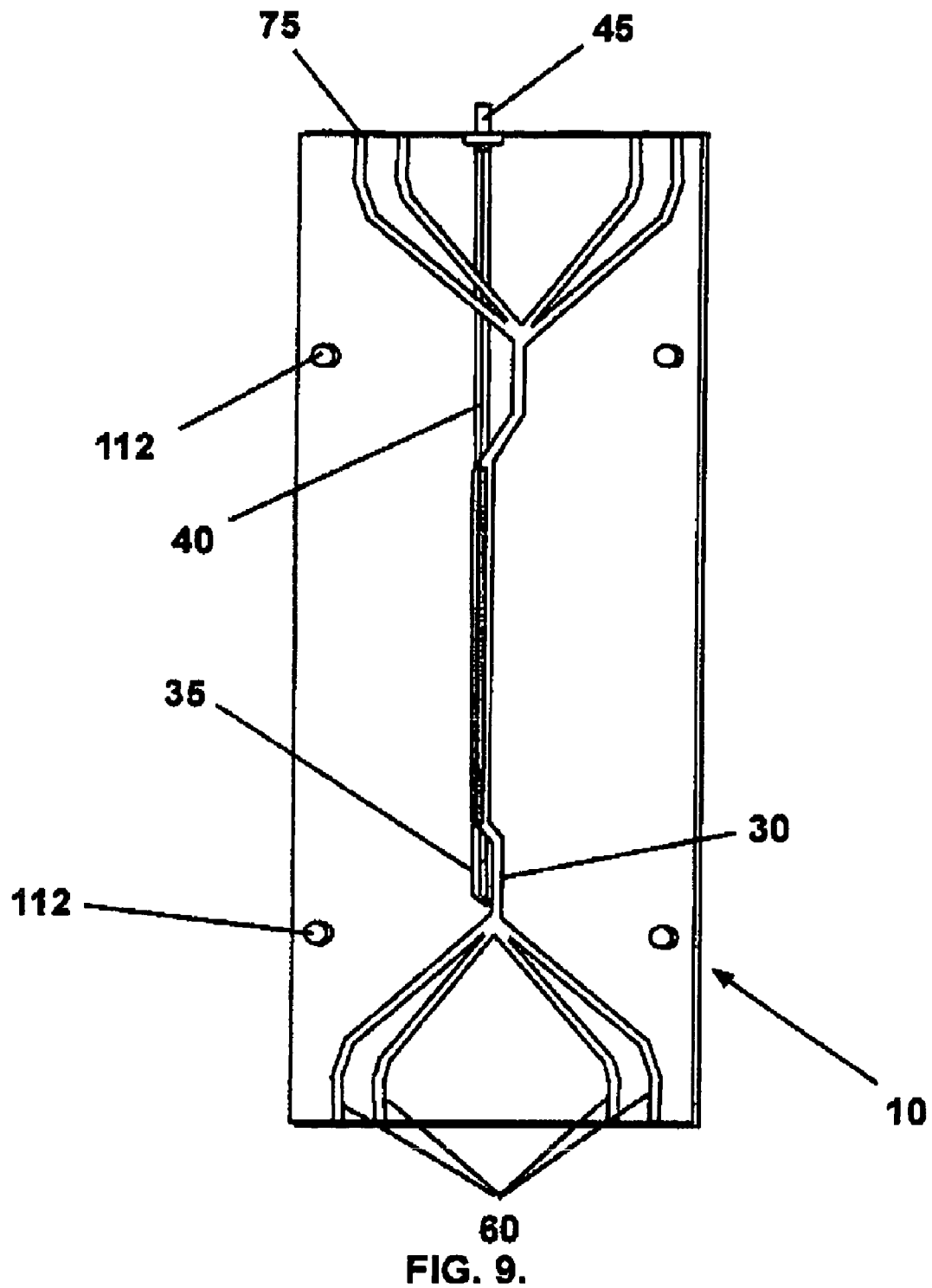
FIG. 9 is a cross-sectional view of the flow cell having a plurality of sample ports, one sample channel, and a plurality of sample outlets.

FIGS. 6–9 show further embodiments of the invention, where the number of sample ports, sample channels, and sample outlets are varied. FIG. 6 depicts an embodiment of the flow cell 10 having one sample port 60, a plurality of sample channels 30, and one sample outlet 75. In addition, the flow cell 10 has a fastening means 112 such that it may be interlocked with other flow cells. An optical fiber channel holder 35 is positioned in an operable relationship to each sample channel 30 such that, for each sample channel 30, there is an optical fiber channel holder 35 positioned in an operable relationship to it. Each optical fiber channel holder 35 has an optical fiber 40 disposed within it. Preferably, each optical fiber 40 has an optical fiber connector 45 attached to an end of the optical fiber 40. This configuration permits multiple readings to be taken on a single sample. FIG. 7 depicts an embodiment of the invention where there is one sample port 60, a plurality of sample channels 30, a plurality of optical fiber channel holders 35 each having an optical fiber 40 disposed therein, and a plurality of sample outlets 75. Each optical fiber 40 has an optical fiber connector 45 affixed to an end of the optical fiber 40. This arrangement allows multiple readings on a single sample with quick removal through the sample outlets 75. FIG. 8 shows an embodiment where the flow cell 10 has a plurality of sample ports 60, one sample channel 30, one optical fiber channel holder 35 having one optical fiber 40 disposed therein and terminating at one end with an optical fiber connector 45, and one sample outlet 75. This configuration allows for sample mixing in the sample channel 30 by allowing different samples to be introduced into the flow cell. Also depicted is a fastening means 112 for assembling the flow cell 10 with other flow cells. The flow cell 10 of FIG. 9 has a plurality of sample ports 60, one sample channel 30, one optical fiber channel holder 35 having one optical fiber 40 disposed therein and terminating at one end with an optical fiber connector 45, and a plurality of sample outlets 75. This configuration allows for mixing of samples in the sample channel 30 plus quick removal of the sample through the sample outlets 75. In addition, fasteners 112 are provided for assembling the flow cell 10 with other flow cells.

Figure 10:
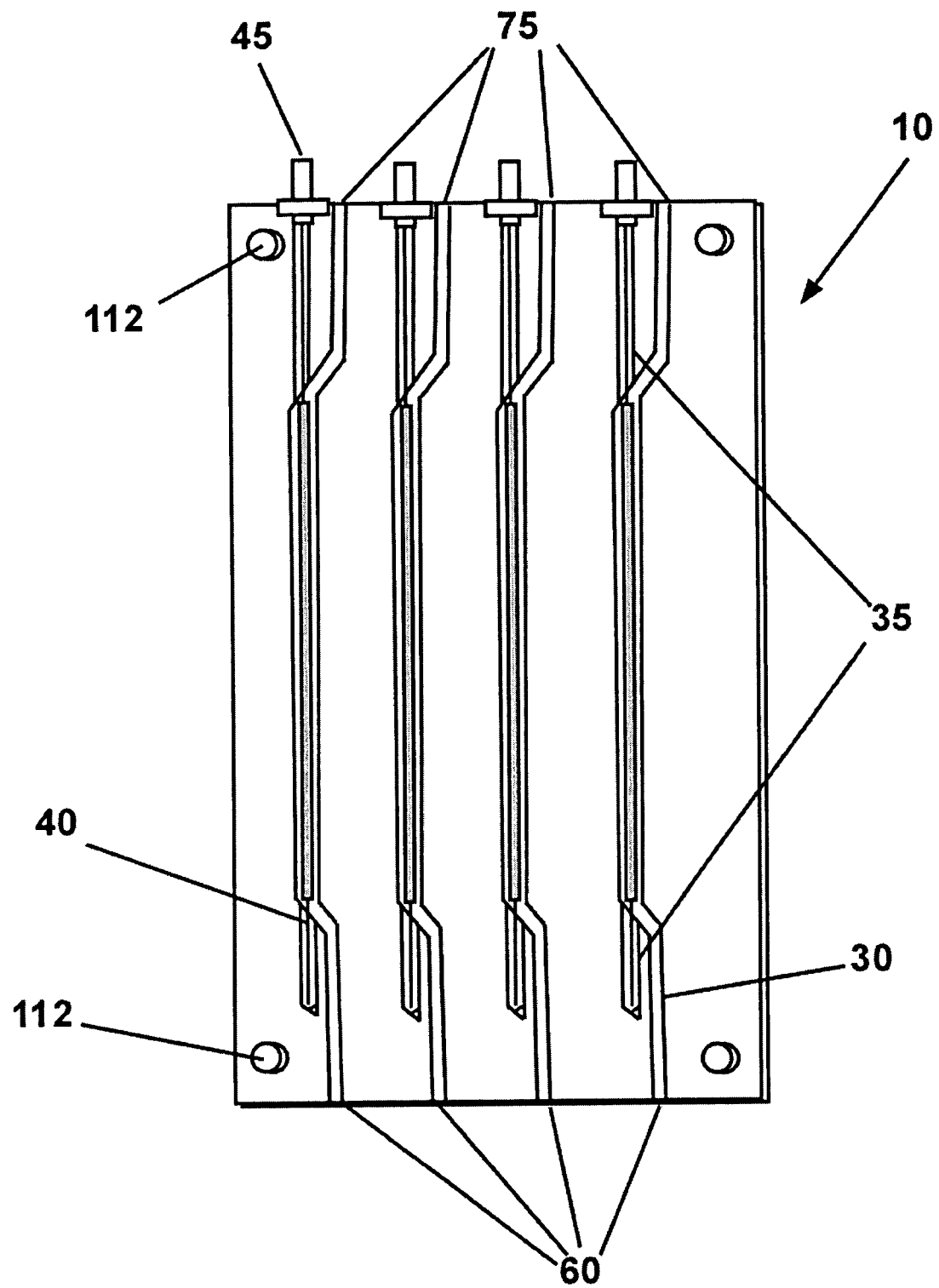
FIG. 10 is a cross-sectional view of the flow cell having a plurality of sample ports, a plurality of sample channels, and a plurality of sample outlets.

FIG. 10 depicts another embodiment of the invention where the flow cell 10 comprises a plurality of sample ports 60; a plurality of sample channels 30; a plurality of optical fiber channel holders 35 having one optical fiber 40 disposed therein and terminating at one end with an optical fiber connector 45, and a plurality of sample outlets 75. This configuration provides the user with the ability to inject many different samples into the flow cell 10 through the sample ports 60 and removal of the samples through the sample outlets 75. In addition, fasteners 112 are provided for assembling the flow cell 10 with other flow cells.

Figure 11A:
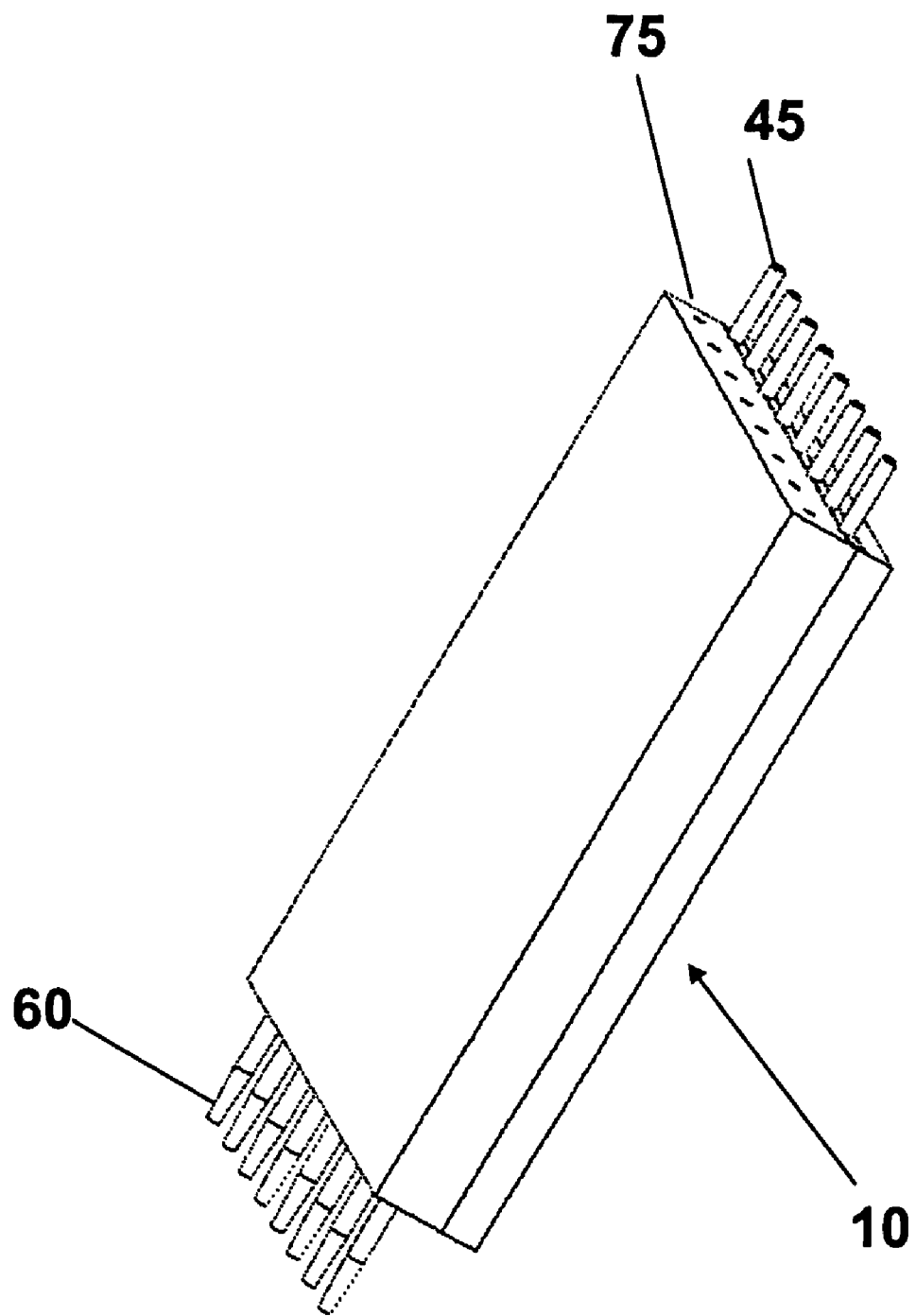
FIG. 11A is a perspective view showing a flow cell array formed by stacking several flow cells together.
Figure 11B:
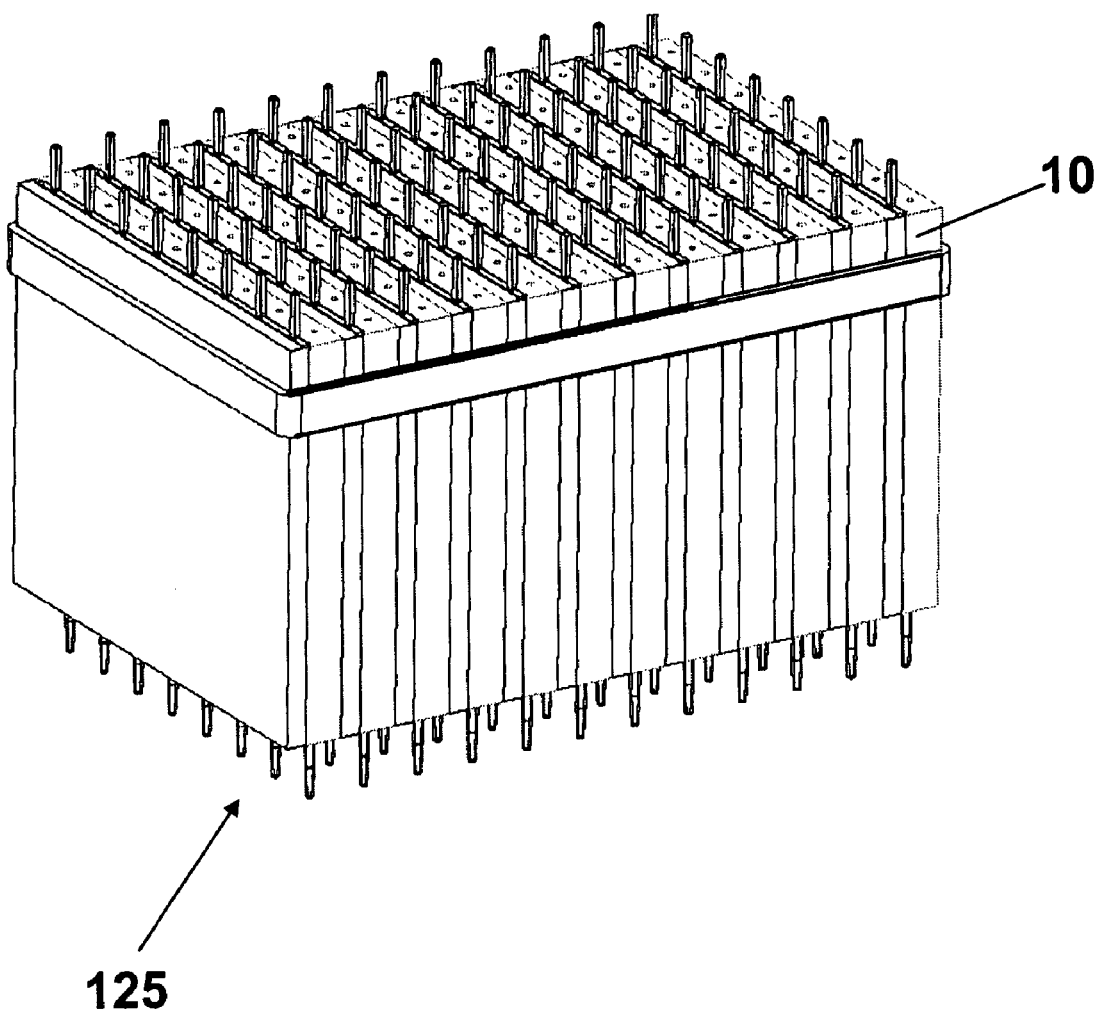
FIG. 11B is a 3-dimensional view showing a stacked flow cell array.

FIGS. 11A and 11B depict how a flow cell array 125 is assembled by stacking various flow cell assemblies 10 together. Each flow cell 10 has a means for interlocking with another flow cell (not shown). In a most preferred embodiment of the invention, the flow cell has at least one sample outlet 75, at least one sample channel (not shown), and 2, 8, 96 384, or 1536 sample ports. Each flow cell has at least one sample port 60. Also depicted is a preferred embodiment where each optical fiber (not shown) terminates with an optical fiber connector 45. When there are multiple sample channels, each channel is spaced apart a distance of less than or about 9 mm. This spacing makes the flow cell compatible wit micro titer plates which are the sample plates used in lift sciences research. The tip volumes and spacing between the tips are designed into the flow cell for microtiter interface. In addition, when the flow cell comprises mating pieces, quadrant sampling can be used to interface with high capacity plates such as 384 and 1536 micro titer plates (FIGS. 11A and 11B).

As a further embodiment to the invention, each sample port has a means to control delivery of the sample into each sample channel. Such means may be any known to those of skill in the art. In particular, the means may be by aspiration, continuous flow, and continuous flow with dwell time when there is no sample outlet. If a sample outlet is part of the flow cell, then the means may also include a continuous loop. When a sample is introduced by aspiration, it undergoes a back and forth motion within the sample channel. Continuous flow involves the movement of the sample into the portion of the sample channel containing the optical fiber in such a way that there is no dynamic recycling of the sample. When there is continuous flow with at least one dwell time, the sample is stopped and held for a certain length of time at the grating location on the optical fiber. Continuous looping of a sample involves moving the sample within the sample channel in such a way that the sample is exposed to the grating on the optical fiber multiple times in a circular or looping configuration such that the sample coming from the sample output is re-fed at the sample port. Alternatively, a sample undergoing continuous looping can undergo a certain dwell time within the sensing area before the sample is re-fed at the sample port.

The samples employed in the present invention may be of any type known to those of skill in the art. In particular, the sample is selected from the group consisting of: a liquid sample, a gas sample; and a complex sample. Combinations of these sample types may also be employed. For example, a liquid sample and a gas sample may be injected into two different sample ports and mixed in the sample channel. A complex sample is defined as a sample that is heterogeneous in composition. Examples of complex samples include but are not limited to: whole blood; serum; grain mixtures; slurries; milk; urine; saliva; and spinal fluid.

The flow cells of the present invention are used to conduct measurement studies on a sample and the flow cell. When the flow cell has no sample outlet, the sample is introduced into the sample port, allowed to flow into each sample channel, and certain characteristics of the sample and the flow cell are measured at the point or points on the optical fiber where the grating is located. After the measurements are completed, the sample is removed from the sample channel through the sample port. Alternatively, if the flow cell contains a sample outlet, the sample is removed through the sample outlet. Various physical characteristics of the sample are measured such as temperature, pressure, refractive index, and pH. These characteristics are based on the relationship of the sample to that of the portion of the flow cell where the optical fiber grating is located.

Alternatively, the flow cells of the present invention are used to measure chemical characteristics of a sample. These changes are based on the actual chemical composition of the sample. For example, the biochemical changes taking place in the sample may be measured. In addition, the biological target concentration, pH, reaction rates and chemical target concentrations may be measured in a sample.

For example, the flow cell may also be used for kinetic studies. Kinetic studies are conducted by treating the optical fiber sensor with ligands that react with targets contained in the sample over a certain time period. The interactions provide information about $K_d$ and $K_a$ coefficients. The flow cell described herein can be used to establish the kinetic binding values of rate of association ($K_{on}$), rate of dissociation ($K_{off}$), and calculate the equilibrium dissociation constant ($K_d$). The following model is used to illustrate the relationship between the values:

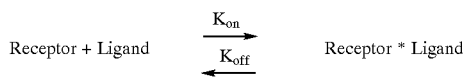

The interaction of the receptor, which is immobilized on the fiber, and the ligand results in a receptor-ligand complex. The rate of this complex formation is the rate of association or $K_{on}$ rate. The formed complex can also dissociate to the free receptor and ligand which is the rate of dissociation or $K_{off}$. When equilibrium is achieved the rate of association is equal to the rate of dissociation and is referred to the equilibrium dissociation constant ($K_d$) and is defined by the ratio $K_{off}/K_{on}$. When the concentration of ligand equals the $K_d$, half the receptors will be occupied at equilibrium. If the receptors have a high affinity for the ligand, the $K_d$ will be low, as it will take a low concentration of ligand to bind half the receptors.

Figure 12:
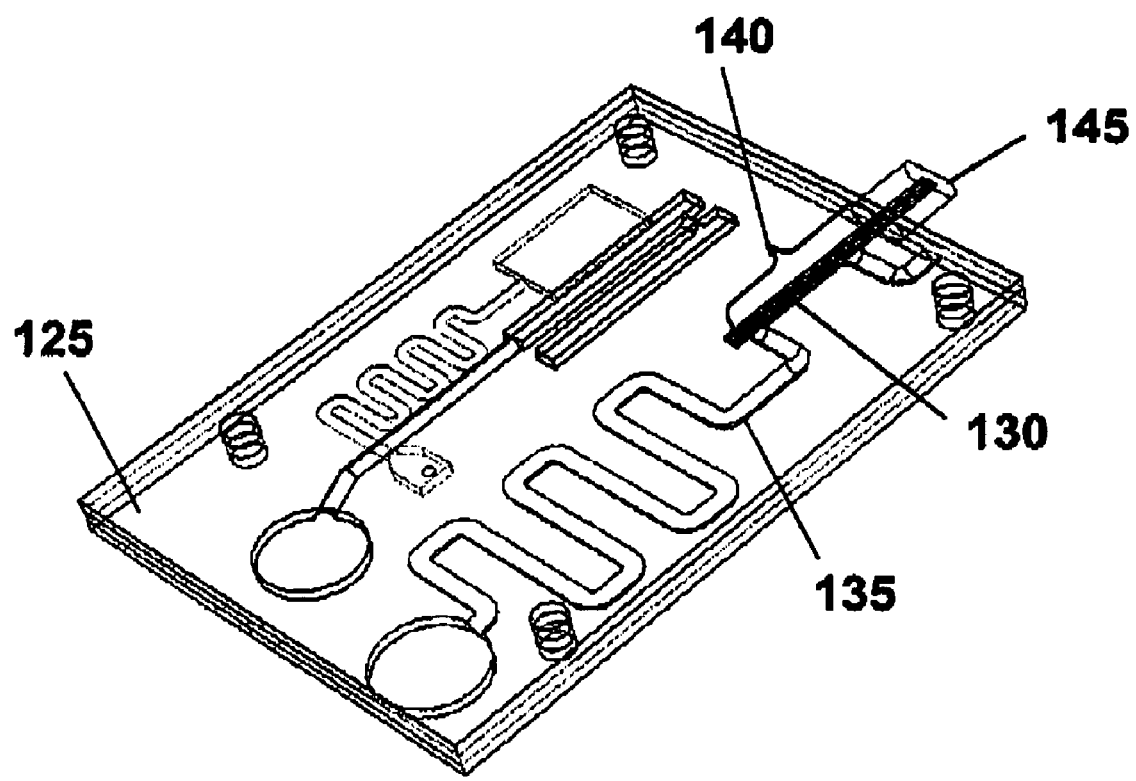
FIG. 12 is a schematic showing a flow cell array integrated with other processes.

FIG. 12 depicts how a flow cell array is integrated with other processes. This integration is useful for lab-on-a-chip type applications. In this embodiment, a flow cell array 125 is integrated with other processes on a chip. Multiple fiber optic grating sensors 130 are in contact with at least one sample channel 135 to form the sensing area 140. An optical fiber connector 145 is disposed on one end of the optical fiber grating sensors 130.

EXAMPLES

Example 1

A Protein A coated sensor was prepared by providing a glass fiber having a long period grating (LPG) disposed therein. The glass fiber was cleaned with a solution of methanol and hydrochloric acid in a 1:1 mixture for one hour at room temperature. The fiber was rinsed with methanol. The fiber was soaked in a 10% solution of (3-Glycidoxypropyl)trimethoxysilane in methanol for one hour at room temperature. The fiber was then rinsed with methanol. Next, the fiber was soaked in a phosphate buffered saline solution, pH 7.4 containing 100 ug/ml Protein A for one hour. The fiber was rinsed with phosphate buffered saline solution, pH 7.4 and stored in the same buffer at 2–8 degrees C.

Example 2

Figure 13:
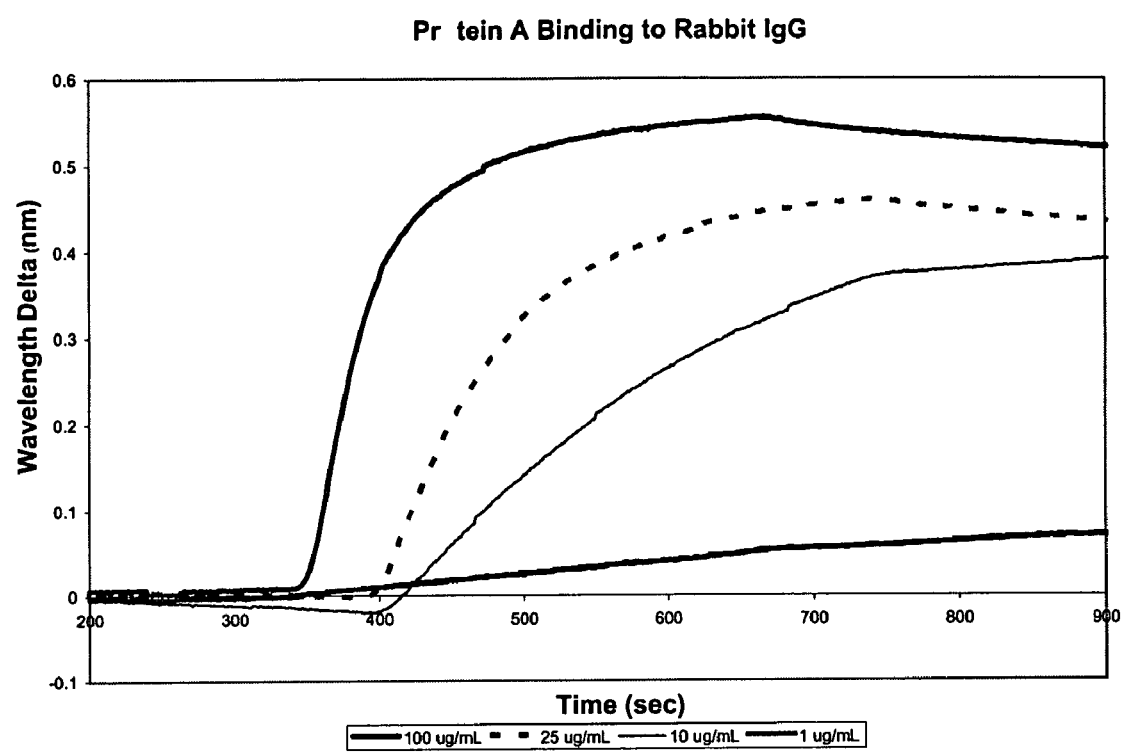
FIG. 13 is a graph depicting the reaction kinetic data when the flow cell of the present invention is in use.

The Protein A coated sensor of Example 1 was used to monitor the response of the sensor to rabbit IgG. The Protein A coated sensor was exposed to a phosphate buffered saline solution, pH 7.4, (PBS) to establish a baseline signal for the sensor. The sensor was then exposed to varying concentrations of rabbit immunoglobulin (IgG, Technical grade available from Sigma) in PBS pH 7.4. As shown in FIG. 13, the rabbit IgG bound to the protein A on the surface on the fiber sensor. The magnitude of the response was dependent upon the concentration of rabbit IgG. To remove any unbound material from the sensor surface, the fiber was exposed to PBS pH 7.4. Next, the fiber was exposed to 10 mM HCl to remove the bound IgG material from the Protein A and to regenerate the fiber for a subsequent assay cycle. Lastly, the fiber was exposed to a PBS pH 7.4 buffer solution to re-establish a baseline and return the sensor to a buffered environment.

Testing for this example took place in a single channel flow cell with multiple repetitions. The flow cell configuration consisted of a 3 part flow cell shown in FIG. 1. The flow cell overall dimensions were [60 mm length×26 mm width×12.6 mm height]. The sample channel was 1 mm outer diameter throughout the flow cell. The long period grating (LPG) sensing element was 1 mm long with a 125 micron outer diameter. The substrate holder that housed the optical fiber channel holder had a sampling window that was 1 mm wide×13 mm long. The substrate holder was 0.5 mm thick. By changing the sensing element surface area and varying the flow cell dimensions, smaller volumes can be achieved during testing.

The above description and drawings are only illustrative of preferred embodiments which achieve the objects, features and advantages of the present invention, and it is not intended that the present invention be limited thereto. Any modification of the present invention which comes within the spirit and scope of the following claims is considered part of the present invention.

What is claimed is:

1. A flow cell comprising:
   a substrate having at least one sample channel integral with at least one optical fiber channel holder;
   wherein each sample channel has a curved portion to deliver fluid to an isolated sensing area;
   wherein each optical fiber channel holder has an optical fiber disposed therein, wherein each optical fiber has at least one grating and wherein each optical fiber is precisely aligned and tensioned in a straight line within each optical fiber channel holder;

wherein the isolated sensing area is defined as an area where each optical fiber grating is proximate to the curved portion of each sample channel; and at least one sample port positioned in an operable relationship to at least one sample channel.

2. A flow cell according to claim 1, wherein the substrate has a monolithic structure.

3. A flow cell according to claim 2, wherein the monolithic structure is either a cylinder or a planar structure.

4. A flow cell according to claim 1, wherein the substrate comprises at least two mating pieces.

5. A flow cell according to claim 4, wherein a plurality of mating pieces form a kit having interchangeable parts whereby the configuration of the flow cell is modified.

6. A flow cell according to claim 4, wherein the mating pieces form either a cylinder or a planar structure.

7. A flow cell according to claim 1, further comprising at least one sample outlet positioned in an operable relationship to at least one sample channel.

8. A flow cell according to claim 7, wherein the substrate has a monolithic structure.

9. A flow cell according to claim 8, wherein the monolithic structure is either a cylinder or a planar structure.

10. A flow cell according to claim 7, wherein the substrate comprises at least two mating pieces.

11. A flow cell according to claim 10, wherein a plurality of mating pieces form a kit having interchangeable parts whereby the configuration of the flow cell is modified.

12. A flow cell according to claim 10, wherein the mating pieces form either a cylinder or a planar structure.

13. A flow cell according to claim 1, wherein the flow cell comprises one sample port and a plurality of sample channels.

14. A flow cell according to claim 1, wherein the flow cell comprises a plurality of sample ports and one sample channel.

15. A flow cell according to claim 7, wherein the flow cell comprises one sample port, a plurality of sample channels, and one sample outlet.

16. A flow cell according to claim 7, wherein the flow cell comprises one sample port, a plurality of sample channels, and a plurality of sample outlets.

17. A flow cell according to claim 7, wherein the flow cell comprises a plurality of sample ports, one sample channel, and one sample outlet.

18. A flow cell according to claim 7, wherein the flow cell comprises a plurality of sample ports, one sample channel, and a plurality of sample outlets.

19. A flow cell according to claim 7, wherein the flow cell has 2 sample channel ports.

20. A flow cell according to claim 7, wherein the flow cell has 8 sample channel ports.

21. A flow cell according to claim 7, wherein the flow cell has 96 sample channel ports.

22. A flow cell according to claim 7, wherein the flow cell has 384 sample channel ports.

23. A flow call according to claim 7, wherein the flow cell has 1536 sample channel ports.

24. A flow cell according to claim 7, wherein each sample channel is spaced apart a distance of less than or about 9 mm.

25. A flow cell according to claim 7, wherein the flow cell is microtiter plate compatible.

26. A flow cell according to claim 1, wherein each sample port has a means to control delivery of the sample into each sample channel.

27. A flow cell according to claim 26, wherein the means to control delivery of the sample into each sample channel is by aspiration.

28. A flow cell according to claim 26, wherein the means to control delivery of the sample into each sample channel is by a continuous flow.

29. A flow cell according to claim 26, wherein the means to control delivery of the sample into each sample channel is by a continuous flow with dwell time.

30. A flow cell according to claim 7, wherein each sample port has a means to control delivery of the sample into each sample channel.

31. A flow cell according to claim 30, wherein the means to control delivery of the sample into each sample channel is by aspiration.

32. A flow cell according to claim 30, wherein the means to control delivery of the sample into each sample channel is by a continuous loop.

33. A flow cell according to claim 30, wherein the means to control delivery of the sample into each sample channel is by a continuous flow.

34. A flow cell according to claim 30, wherein the means to control delivery of the sample into each sample channel is by a continuous flow with dwell time.

35. A flow cell according to claim 7, wherein the sample is selected from the group consisting of: a liquid sample; a gas sample; and a complex sample.

36. A flow cell according to claim 1, wherein the grating is a long period grating.

37. A flow cell according to claim 36, wherein a reactive coating is positioned in an operable relationship to the long period grating.

38. A flow cell according to claim 1, wherein the grating is a Bragg grating.

39. A flow cell according to claim 7, wherein the grating is a long period grating.

40. A flow cell according to claim 39, wherein a reactive coating is positioned in an operable relationship to the long period grating.

41. A flow cell according to claim 7, wherein the grating is a Bragg grating.

42. A flow cell kit comprising an upper substrate having at least one curved sample channel for delivering a sample to an isolated sensing area and at least one sample port disposed therein; at least one optical fiber channel holder having an optical fiber disposed therein wherein each optical fiber has at least one grating disposed therein wherein each optical fiber is precisely aligned and tensioned in a straight line within each optical fiber channel holder; wherein the optical fiber channel holder has a means to connect to the upper substrate to form a unit wherein the isolated sensing area is defined as an area where the grating is proximate to the curved portion of the sample channel; and a lower substrate having a means to connect to the optical fiber channel holder on a side opposite from the upper substrate.

43. A flow cell kit according to claim 42, wherein the upper and lower substrates each have a means to interconnect with each other to form an array.

44. A flow cell according to claim 11, comprising an upper section having at least one sample channel and at least one sample port; a middle section comprising an optical fiber channel holder having an optical fiber disposed therein; a lower section serving as a support base; wherein the upper section and the lower section are counter-sunk to permit critical alignment of the optical fiber channel holder with each sample channel.

* * * * *